(12) United States Patent
Wakeman et al.

(10) Patent No.: US 7,086,280 B2
(45) Date of Patent: Aug. 8, 2006

(54) AERATION SENSING DEVICE

(75) Inventors: Russell J. Wakeman, Canton, MI (US); Wayne A. Thelen, Ypsilanti, MI (US)

(73) Assignee: Ricardo, Inc., Van Buren Township, MI (US)

( * ) Notice: Subject to any disclaimer, the term of this patent is extended or adjusted under 35 U.S.C. 154(b) by 132 days.

(21) Appl. No.: 10/679,883

(22) Filed: Oct. 6, 2003

(65) Prior Publication Data

US 2005/0072210 A1  Apr. 7, 2005

(51) Int. Cl.
*G01N 30/62* (2006.01)
*G01N 33/26* (2006.01)

(52) U.S. Cl. .................... 73/61.61; 73/53.05
(58) Field of Classification Search ........... 73/53.05, 73/61.41, 61.61; 324/448
See application file for complete search history.

(56) References Cited

U.S. PATENT DOCUMENTS

| 4,599,888 | A | | 7/1986 | Hufton et al. |
| 5,861,811 | A | * | 1/1999 | Lease et al. ............... 340/618 |
| 6,553,812 | B1 | * | 4/2003 | Park et al. ................. 73/54.01 |
| 6,867,603 | B1 | * | 3/2005 | Nicholson et al. ......... 324/698 |

* cited by examiner

*Primary Examiner*—Hezron Williams
*Assistant Examiner*—John Fitzgerald
(74) *Attorney, Agent, or Firm*—Butzel Long (57) ABSTRACT

A system for detecting aeration in a lubricant includes a sensor having a pair of spaced apart concentric rings forming a first capacitor through which the lubricant flows and a capacitor segment forming a second capacitor with the outer ring. The capacitors are connected in a balanced bridge circuit and the second capacitor is constructed to remove gas entrapped in the lubricant present in the second capacitor so that the bridge becomes unbalanced indicating gas entrapped in the lubricant flowing through the first capacitor.

28 Claims, 6 Drawing Sheets

AERATION SENSING DEVICE

BACKGROUND OF THE INVENTION

The present invention relates generally to an apparatus for detecting gas entrapped in a liquid lubricating system, and more specifically, to an aeration sensing device for detecting gas entrapped in the engine oil of an internal combustion engine.

Engine oil has been used in engine systems to lubricate moving parts such as pistons, piston rods, compression rings, and other engine components to reduce friction and heat build up between the moving parts and an engine block. Contaminants or foreign substances found in the engine oil can inherently damage an engine system. Gas, such as air or combustion products, entrapped in the lubricant can also result in improper or inadequate lubrication of the engine components and can damage engine components including the oil pump.

Vehicle systems utilize various sensors within a vehicle to monitor whether an engine is operating within normal operating parameters. One type of such sensors is an oil pressure sensor that monitors the oil pressure exiting from the oil pump. If the oil pressure goes below or above a predetermined operating range, a warning indicator is displayed to the operator of a vehicle informing the operator of the improper operating condition that is occurring. However, oil pressure sensors are used only for detecting the oil pressure of the engine system, and such sensors are not indicative of aeration caused by gas entrapped in the engine oil. Aeration within the engine oil may not necessarily affect the oil pressure, but the aeration could still cause damage to the engine components. An aeration detection system as described in U.S. Pat. No. 4,599,888 utilizes a rod encased within a cylinder for monitoring the capacitance with oil flowing between the rod and the cylinder wall. However, other impurities or contaminants within the engine oil could change the capacitance. The system in the referenced patent does not differentiate between contaminants in the lubricant causing a capacitance change and aeration in the system causing a capacitance change.

SUMMARY OF THE INVENTION

The present invention concerns a system for detecting aeration in a lubricant which system includes a sensor having a pair of spaced apart concentric rings forming a first capacitor through which the lubricant flows and a capacitor segment forming a second capacitor with the outer ring. The capacitors are connected in a balanced bridge circuit and the second capacitor is constructed to remove gas entrapped in the lubricant present in the second capacitor so that the bridge becomes unbalanced indicating gas entrapped in the lubricant flowing through the first capacitor.

The aeration sensing system comprises: a non-conductive sensor body having opposed first and second ends; a first capacitor positioned within the sensor body and having spaced apart plates forming a first gap; a lubrication flow path formed in the sensor body between the first and second ends and including the first gap; a second capacitor positioned within the sensor body and having spaced apart plates forming a second gap in fluid communication with the lubrication flow path, the second gap being in the form of a dead-end cavity; a bridge circuit having the first and second capacitors connected in associated legs thereof; and a signal generator connected to and generating an input signal at an input of the bridge circuit, the bridge circuit being balanced when non-aerated lubricating fluid is flowing in the lubrication path and being unbalanced when aerated lubricating fluid is flowing in the lubrication path.

The signal generator can be an oscillator and the system includes a demodulator connected to an output of the bridge circuit for generating an output signal. The plates of the first capacitor are first and second conductive rings positioned concentrically in said sensor body and the plates of the second capacitor are the second conductive ring and a conductive segment positioned in the sensor body. The first and second rings and the segment can be formed of copper material and the sensor body can be formed of a plastic phenolic material.

DESCRIPTION OF THE DRAWINGS

The above, as well as other advantages of the present invention, will become readily apparent to those skilled in the art from the following detailed description of a preferred embodiment when considered in the light of the accompanying drawings in which.

DESCRIPTION OF THE PREFERRED EMBODIMENT

Figure 1:
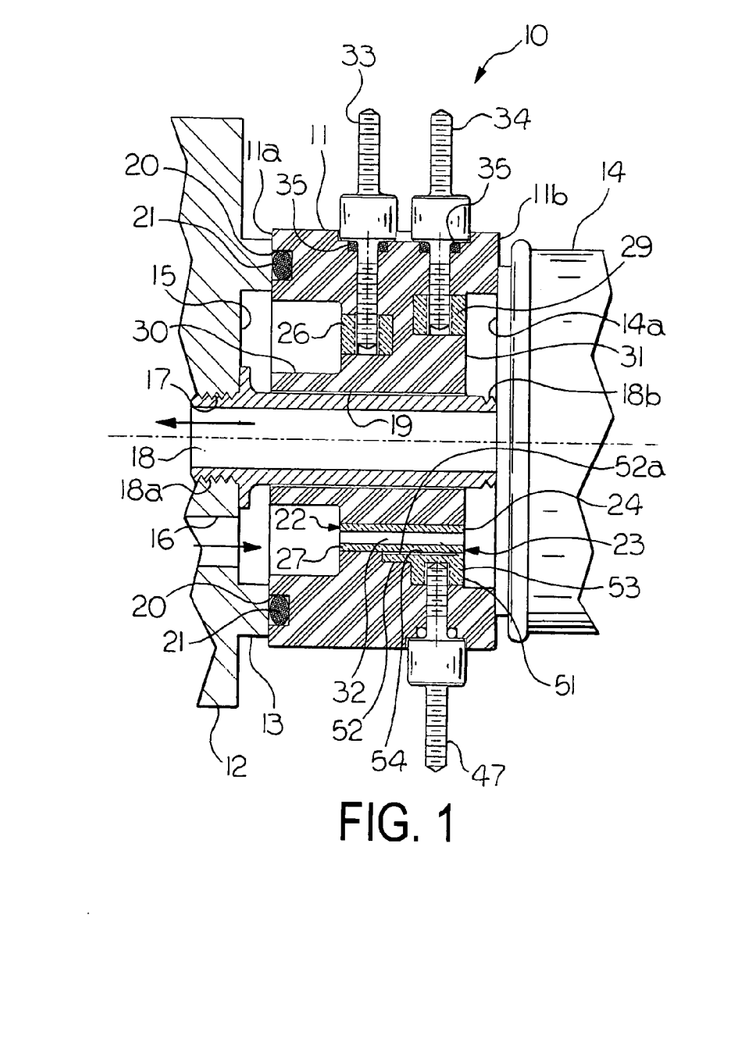
FIG. 1 is a side elevation view of an aeration sensing device according to a first preferred embodiment of the present invention in cross section taken along the line 1—1 in FIG. 2.
Figure 2:
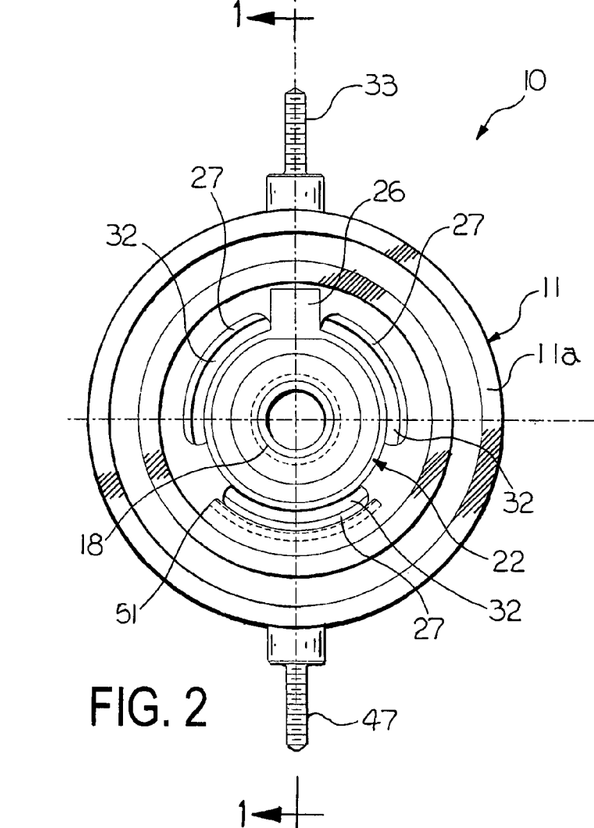
FIG. 2 is an end view of the aeration sensing device shown in FIG. 1.

Referring now to the drawings and particularly to FIGS. 1 and 2, there is shown an aeration sensing device 10 for detecting gas entrapped in a liquid lubricating system. The aeration sensing device 10 is mounted between a filtration device 14 (e.g. an oil filter) and a filtration device mount 12 (e.g. an engine oil filter mount). The aeration sensing device 10 includes a generally cylindrical sensor body 11 that is produced from a nonconductive material such as plastic phenolic. Alternatively, the sensor body 11 can be made from any other high temperature nonconductive composite material. The filtration device mount 12 has a lubrication outlet circuit or passageway 16 formed therein open to a facing surface 15 of the mount. The circuit 16 allows lubricant to flow from a lubricating area (not shown) to the aeration sensing device 10 and on to the filtration device 14. A return passageway or lubrication inlet circuit 17 is formed in the mount 12 and is open to the surface 15 for allowing filtered lubricant to return from the filtration device 14 through the sensing device 10 to the lubrication area (not shown). The surface 15 is surrounded by an outwardly extending flange 13.

The return path includes a tubular conduit 18 having an externally threaded first end 18*a* threadably engaged with an internal thread formed in the opening of the inlet circuit 17. The conduit 18 extends through an axial aperture or central bore 19, formed in the body 11, to an externally threaded second end 18*b* that threadably engages the filtration device 14. Although the conduit 18 is shown and described as threadably engaging the mount 12 and the filtration device 14, other methods of fastening known in the art may be utilized. An internal diameter of the central bore 19 is slightly larger than an outer diameter of the return conduit 18 to allow the aeration sensing device body 11 to slip fit over the conduit and rotate thereabout. The conduit 18 is first threaded into the open end of the inlet circuit 17 and then receives the sensing device 10. The sensor body 11 has a first end 11*a* that abuts the flange 13. Then the filtration device 14 is threaded onto the second end 18*b* of the conduit 18 and rotated to tighten an end 14*a* of the filtration device against a sensor body second end 11*b* to seal the flange 13 to the surface 11*a* and to seal the end 14*a* to the surface 11*b*. An annular groove 20 can be formed in the surface 11*a* to retain an O-ring 21 for better sealing at the abutting end 11*a* and the flange 13. Typically, the filtration device 14 has an annular groove (not shown) formed in the surface 14*a* to retain an O-ring (not shown) for better sealing at the abutting ends 11*b* and 14*a*.

Alternatively, the conduit 18 can be divided for threaded engagement with the corresponding ends of the central aperture 19. Thus, as oriented in FIG. 1, a left portion of the conduit 18 would threadably engage the aperture 19 at the first end 11*a* and a right portion would threadably engage the aperture 19 at the second end 11*b*.

A smaller diameter first conductive capacitor ring 22 and a larger diameter second conductive capacitor ring 23 are press fit into the sensor body 11. Alternatively, the sensor body 11 may be injection molded and the first and second rings 22 and 23 may be overmolded into the sensor body 11. Both of the first and second rings 22 and 23 are made from a suitable material such as copper tubing and share a common axis with the sensor body 11 and the central aperture 19. Other types of conductive material may be utilized in place of the copper tubing.

Figure 3:
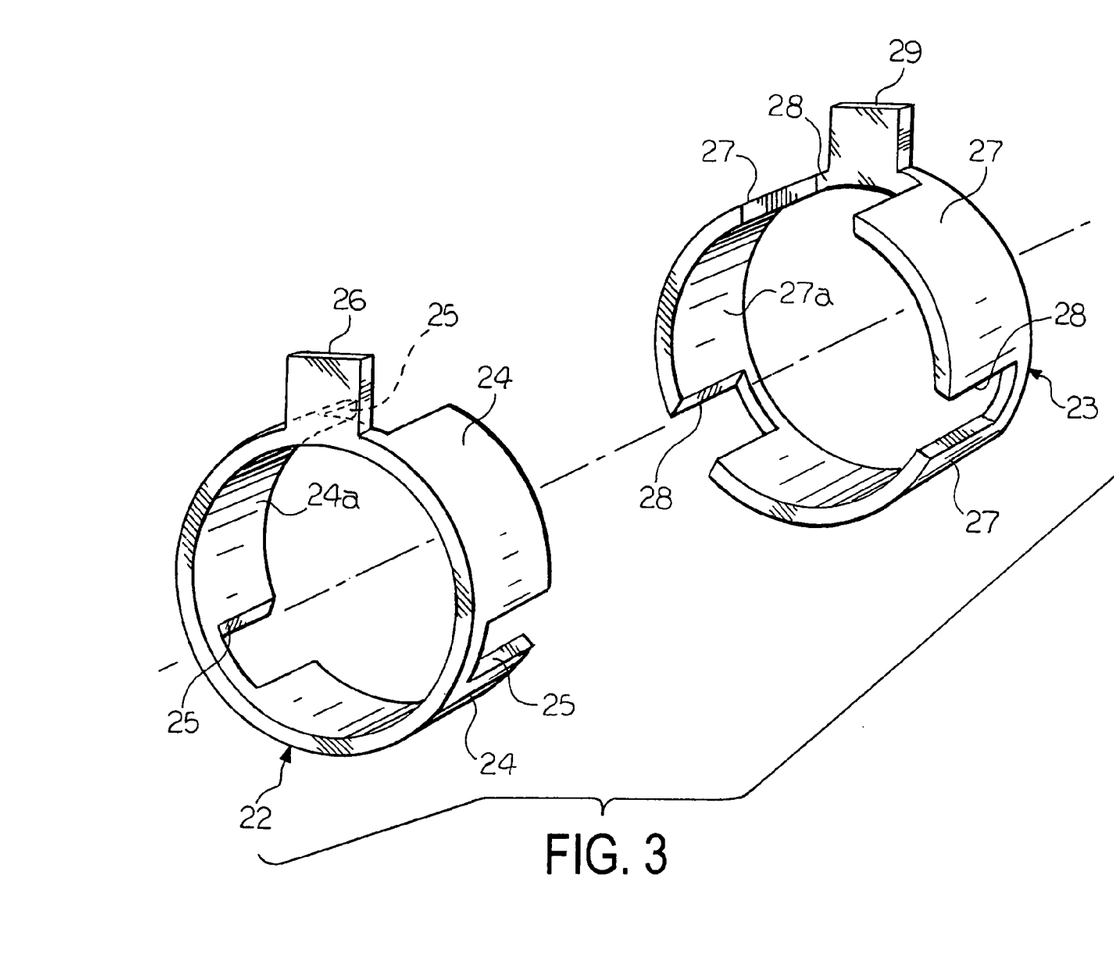
FIG. 3 is a perspective view of the first and second capacitance plates shown in FIG. 1.

In the preferred embodiment, as best shown in FIG. 3, the first ring 22 includes an axially extending wall formed of a plurality of arc shaped plates or wall segments 24 extending axially along the common axis with adjacent wall segments separated by one of a plurality of slots or openings 25. A terminal lug 26 extends radially from the first ring 22. The second ring 23 is of similar construction to the first ring 22 and has a plurality of arc shaped plates or wall segments 27 extending axially along the common axis with adjacent partition walls separated by one of a plurality of slots or openings 28 and a terminal lug 29 extending radially from the second ring 23. The first ring 22 is positioned in an annular groove 30 formed in the first end 11*a* and the walls 24 extend through the body 11 to a circular recess 31 formed in the second end 11*b*. Each of the walls 24 is aligned with an associated one of the walls 27 in a pair to form a gap 32 therebetween permitting fluid flow between the walls from the groove 30 to the recess 31. The gaps 32 are arcuate in shape and correspond in number to the number of pairs of walls. Since the lubricating fluid can become electrically conductive through additives that have metallic components and/or combustion debris from engine operation, the surfaces of the rings 22 and 23 exposed to the lubricating fluid can be covered with a suitable non-conductive material, 22*a* and 23*a* respectively, to prevent shorting of the capacitor plates. The non-conductive material, 22*a* and 23*a* can be, for example, a powder coat material. Typical powder coat materials are polyester, epoxy, urethane, and mixtures thereof depending upon the desired characteristics.

Preferably, the first and second rings 22 and 23 each include three of the wall segments 24 and 27 respectively. However, more or less segments can be provided. One of the slots 27 is aligned with the terminal lug 29 so that the terminal lug 26 can extend upwardly through that slot when the rings 22 and 23 are inserted into the body 11.

A first terminal 33 extends radially into the sensor body 11 and is threaded into the terminal lug 26 for electrical connection to the first ring 22. Similarly, a second terminal 34 extends radially into the sensor body 11 and is threaded into the terminal lug 29 for electrical connection to the second ring 23. Each of the terminals 33 and 34 is sealed at the exterior of the body 11 by an associated O-ring 35 for maintaining a seal against leakage either into or out of the body.

Figure 4A:
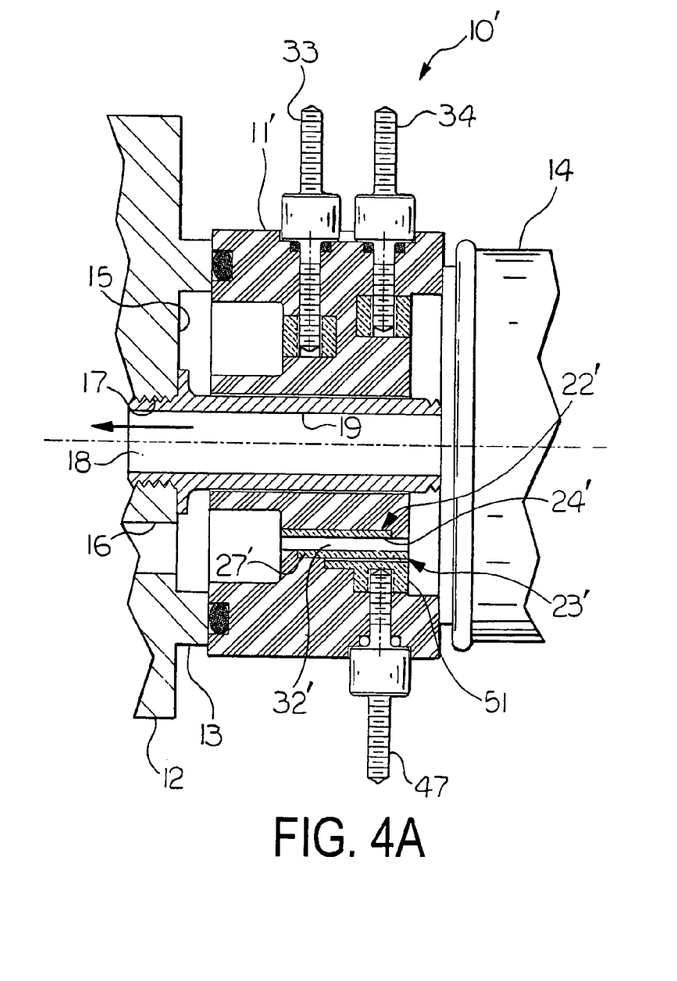
FIG. 4A is a view similar to FIG. 1 of an aeration sensing device according to a second preferred embodiment of the present invention in cross section taken along the line 4A—4A in FIG. 5.
Figure 4B:
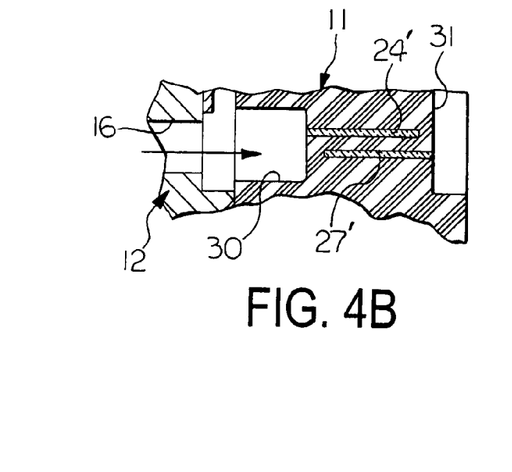
FIG. 4B is an enlarged cross-sectional view taken along the line 4B—4B in FIG. 5.
Figure 5:
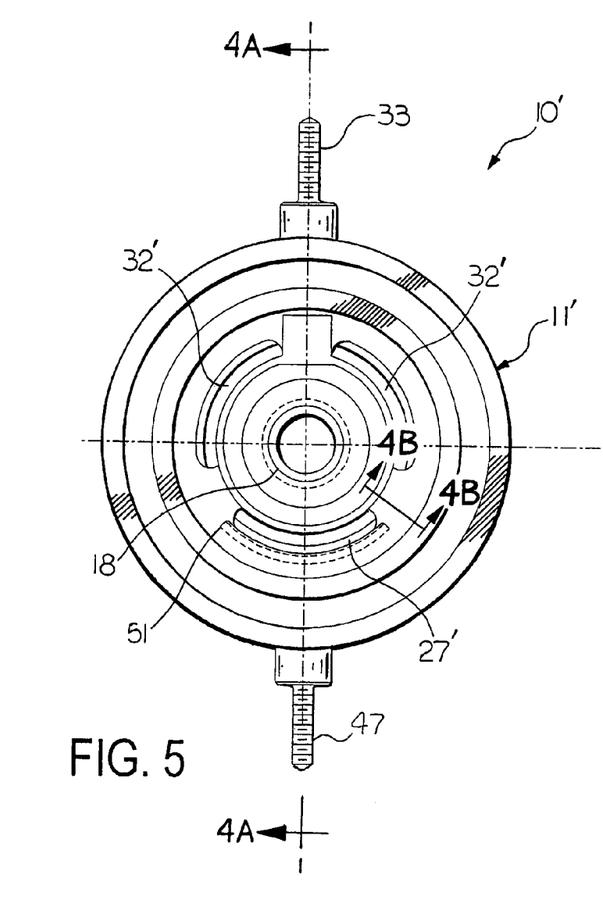
FIG. 5 is a view similar to FIG. 2 of the aeration sensing device shown in FIGS. 4A and 4B.
Figure 6:
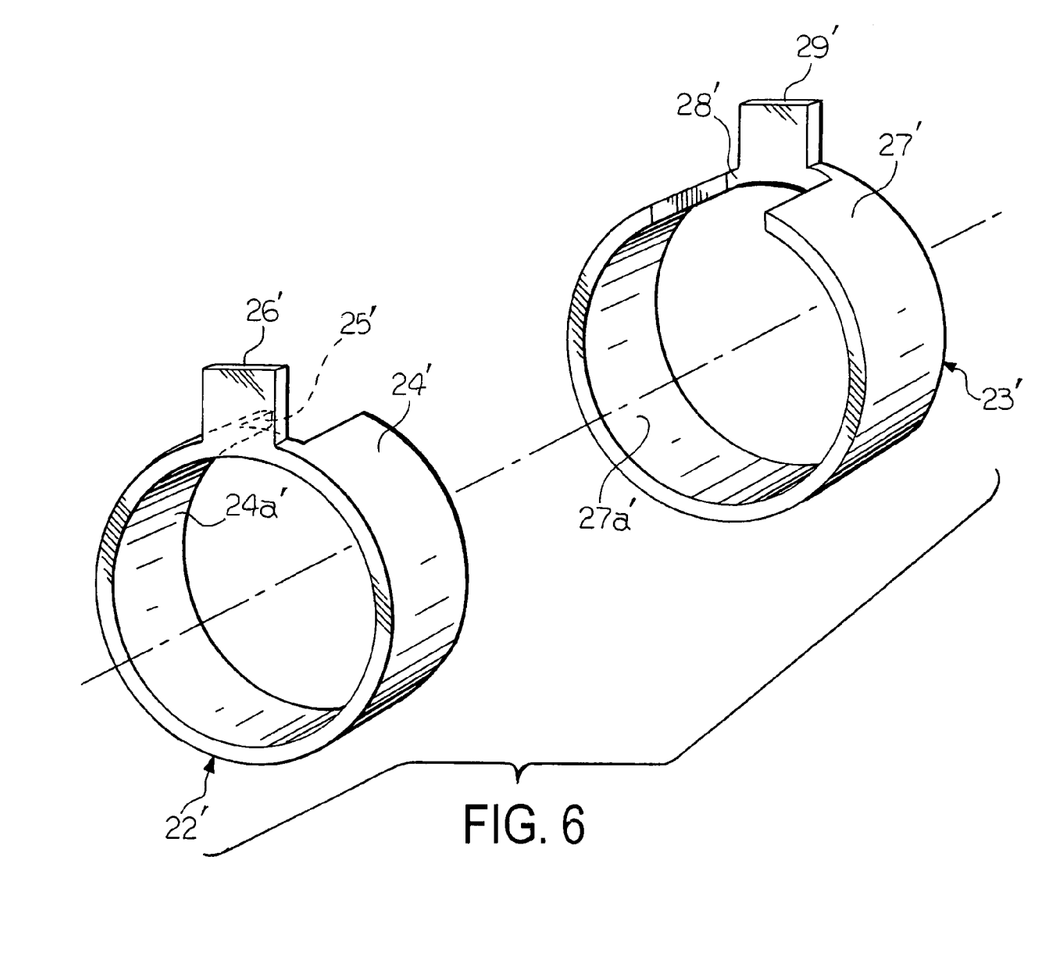
FIG. 6 is a perspective view of the first and second capacitance plates shown in FIG. 4A.

In a second preferred embodiment sensing device 10', shown in FIGS. 4A, 4B, 5 and 6, both the first and second rings 22' and 23' include a substantially continuous wall extending axially along the common axis as shown in FIG. 6. The first ring 22' has a wall 24' interrupted by a single slot 25' adjacent to a terminal lug 26'. The second ring 23' has a wall 27' interrupted by a single slot 28' adjacent to a terminal lug 29' for receiving the terminal adapter 26'. Both of the walls 24' and 27' extend only a portion of the axial length into the sensor body 11. As shown in FIG. 4B, the wall 24' terminates short of the bottom surface of the recess 31 and the wall 27' terminates short of the bottom surface of the groove 30. Otherwise the body 11' could not be formed as an integral one-piece molded structure. The surfaces of the rings 22' and 23' exposed to the lubricating fluid can be covered with a suitable non-conductive material, 22*a*' and 23*a*' respectively, to prevent shorting of the capacitor plates.

Figure 7:
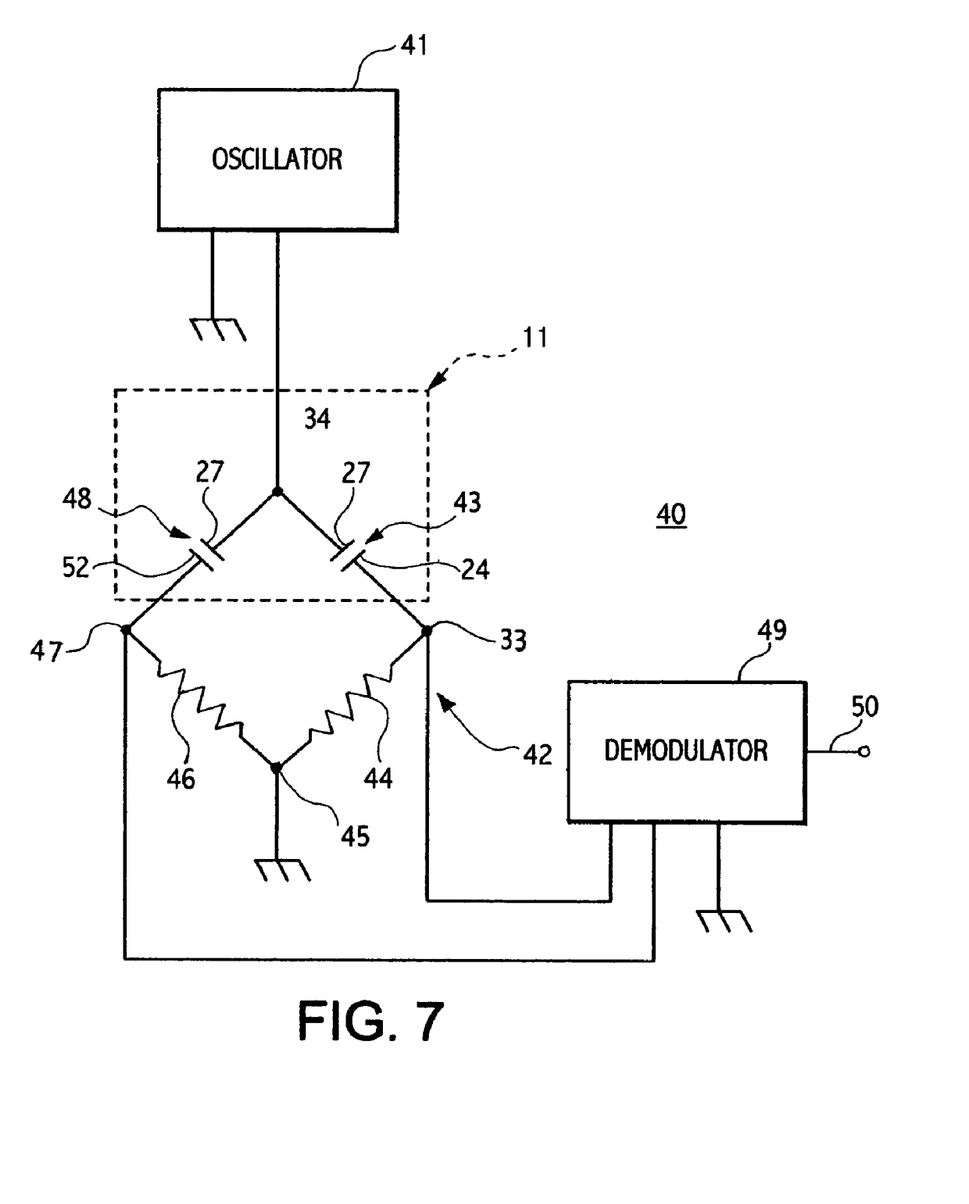
FIG. 7 is an electrical diagram of an aeration sensing system incorporating the sensors according to the present invention.

The engine lubricant filtration circuit 16 provides lubricant to the filtration device 14 via the aeration sensing device 10 (10') for filtering contaminants from the lubrication. The lubricant is forced under pressure through the arcuate flow passages or gaps 32 (32') to the filtration device 14. The aeration sensing device 10 (10') is included in an aeration sensing system 40 (shown in FIG. 6) in accordance with the present invention. A signal generator, such as an oscillator 41, has an output electrically connected to the sensor second terminal 34 and generates an input signal (e.g. oscillating voltage of fixed amplitude and frequency). The sensor first terminal 33 and the sensor second terminal 34 are connected at opposite ends of a first leg of a bridge circuit 42. The first leg includes an oil aeration capacitor 43 with plates formed by the walls 24 (24') and 27 (27'). A second leg of the bridge circuit 42 includes a first resistor 44 connected between the sensor first terminal 33 and a ground terminal 45. A third leg of the bridge circuit 42 includes a second resistor 46 connected between the ground terminal 45 and a sensor third terminal 47. A fourth leg of the bridge circuit 42 includes a compensating capacitor 48 connected between the sensor second terminal 34 and the sensor third terminal 47. The terminals 34 and 45 are the inputs to the bridge circuit 42 and the terminals 33 and 47 are the outputs at which an output signal is generated. A demodulator 49 has a pair of inputs connected to the terminals 33 and 47 and an output 50 at which a sensor output signal is generated.

As the lubricant passes between the walls 24 (24') and 27 (27'), the first capacitor 43 will have a capacitance value that is proportional to the areas of the plurality of partition walls (e.g., capacitance plates) and the net dielectric properties of the lubricant and the gap 32 between them. The demodulator 49 receives the output signal from the bridge 42 and converts it to an output signal (e.g., a DC signal) that is proportional to the capacitance value associated with the lubricant flowing through the first capacitor 43. Since the lubricant has a known dielectric constant, changes in the capacitance of the first capacitor 43 will be reflected in the signal at the output 50. However, any detected changes in the capacitance of the first capacitor 43 can be a direct result of either lubricant specifications, contaminants, aeration entrapped in the lubricant, deterioration of the lubricant, fuel dilution, or temperature affects. Since the change in capacitance may be a direct effect from any one of the sources mentioned previously, aeration entrapped in the lubricant cannot be positively identified as the cause of the change in the capacitance. To differentiate whether the change in the capacitance is a direct result of either the aeration or one of the other sources, the second capacitor 48 is added to the system to compensate for changes to the capacitance of the first capacitor 43 caused by sources other than aeration.

As shown in FIGS. 1 and 2, a capacitor segment 51 is retained in the body 11 and has an arcuate plate or wall 52 spaced from one of the walls 27. The segment 51 is provided with a terminal lug 53 extending radially from the wall 52 and electrically connected to the third terminal 47. The wall 52 can be made of copper and cooperates with the adjacent wall 27 to form the plate of the second capacitor 48. A gap between the walls 27 and 52 forms a chamber for receiving the lubricant open to the recess 31 at one end and closed by the body 11 at the opposite end to function as a dead-end cavity. The distance between the capacitance plates and the surface area of the capacitance plates of the second capacitor 48 defines a capacitance equal to the capacitance of the first capacitor 43 when non-aerated lubricant is present in each capacitor. The surfaces of the capacitor segment 51 exposed to the lubricating fluid can be coated with a non-conductive material 52a in the manner described above.

The arc shaped chamber 54 is arranged so that the lubricant within the dead end cavity is in a substantially stagnant area (i.e., no flow in or out). The dead-end cavity is arranged to be filled with lubricant from the main flow, however, the dead-end cavity will hold the lubricant for a sufficient duration to allow the lubricant to de-aerate. During installation of the sensor 10 (10'), the chamber 54 is radially positioned at the lowest point by rotating the body 11 (11') about the conduit 18 so that the ends of the arc are the highest points and any gas entrapped within this chamber can easily escape to the recess 31. As a result, any difference between the capacitance of the first capacitor 43 and the capacitance of the second capacitor 48 is due to aeration of the lubricant flowing through the first capacitor 43.

The resistors 44 and 46 are of equal value and the bridge 42 is balanced when the capacitance values of the first capacitor 43 and second capacitor 48 are equal. Thus, the terminals 33 and 47 will be at equal potential and there is no output signal for the demodulator 49 to sense. When the capacitance of the first capacitor 43 changes due to aeration of the lubricant, the bridge 42 becomes unbalanced and a bridge output signal is generated to the demodulator 49. If the dielectric constant of the lubricant changes due to some factor other than aeration, the first capacitor 43 and the second capacitor 48 will change capacitance by an equal amount and the bridge 42 will stay balanced. The first capacitor 43 and the second capacitor 48 cause the sensing device 10 (10') to stay in calibration even though the dielectric constant of the lubricating fluid changes during operation. Furthermore, the bridge 42 has a better immunity to the electrical noise generated by an operating vehicle.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. An aeration sensing device for detecting aeration in a fluid comprising:

a non-conductive sensor body having opposed first and second ends;

a conductive first ring positioned within said sensor body, said first ring including a first wall;

a conductive second ring positioned within said sensor body and extending concentrically around said first ring, said second ring including a second wall adjacent to and spaced from said first wall to form a first gap, said first and second walls being plates of a first capacitor; and a fluid flow path formed in said sensor body between said first and second ends and including through said first gap, whereby when a fluid is introduced to said fluid flow path, the fluid flows through said first gap to said second end and serves as a dielectric material defining a capacitance value for said first capacitor, and further including a conductive segment positioned within said sensor body radially outwardly from said second ring and including a third wall adjacent to and spaced from said second wall to form a second gap in fluid communication with said fluid flow path, said second gap being in the form of a dead-end cavity, said second and third walls being plates of a second capacitor whereby when aerated fluid is flowing in said fluid flow path, a portion of the aerated fluid flows into said second gap and becomes de-aerated serving as a dielectric material establishing a contrasting baseline dielectric constant for said fluid and defining a capacitance value for said second capacitor.

2. The device according to claim 1 wherein said sensor body is generally cylindrical and said first and second rings extend about a longitudinal axis of said sensor body.

3. The device according to claim 2 including a first terminal electrically connected to said first ring, a second terminal electrically connected to said second ring and a third terminal electrically connected to said segment, said first through third terminals extending radially through said sensor body.

4. The device according to claim 1 wherein said first and second walls each are formed as a plurality of wall segments extending axially and being separated by slots.

5. The device according to claim 1 wherein said first and second walls each are interrupted by a single slot.

6. The device according to claim 1 wherein said first ring has a radially outwardly extending terminal lug and said second wall has a slot formed therein receiving said terminal lug.

7. The device according to claim 1 wherein said sensor body has a central aperture formed therein permitting the fluid to flow from said second end to said first end of said sensor body.

8. The device according to claim 7 including a conduit extending through said central aperture, a first end of said conduit adapted to attach to a filtration device mount and a second end of said conduit adapted to attach to a filtration device.

9. An aeration sensing device for detecting aeration in a lubricating fluid comprising:
a generally cylindrical non-conductive sensor body having opposed first and second ends;
a conductive first ring positioned within said sensor body, said first ring including a first wall;
a conductive second ring positioned within said sensor body and extending concentrically around said first ring, said second ring including a second wall adjacent to and spaced from said first wall to form a first gap, said first and second walls being plates of a first capacitor;
a lubrication flow path formed in said sensor body between said first and second ends and including said first gap;
a conductive segment positioned within said sensor body radially outwardly from said second ring and including a third wall adjacent to and spaced from said second wall to form a second gap in fluid communication with said lubrication flow path, said second gap being in the form of a dead-end cavity, said second and third walls being plates of a second capacitor,
whereby when an aerated lubricating fluid is introduced to said lubrication flow path at said first end, the lubrication fluid flows through said first gap to said second end and serves as a dielectric material defining a capacitance value for said first capacitor and a portion of the aerated lubricating fluid flows into said second gap and becomes de-aerated serving as a dielectric material defining a capacitance value for said second capacitor.

10. The device according to claim 9 wherein said first and second walls each are formed as a plurality of wall segments extending axially and being separated by slots.

11. The device according to claim 9 wherein said first and second walls each are interrupted by a single slot.

12. The device according to claim 9 wherein surfaces of said first and second rings and said segment exposed to the lubricating fluid are coated with an electrically non-conductive material.

13. An aeration sensing system for detecting aeration in a lubricating fluid comprising:
a non-conductive sensor body having opposed first and second ends;
a first capacitor positioned within said sensor body and having spaced apart plates forming a first gap;
a lubrication flow path formed in said sensor body between said first and second ends and including said first gap;
a second capacitor positioned within said sensor body and having spaced apart plates forming a second gap in fluid in communication with said lubrication flow path, said second gap being in the form of a dead-end cavity;
a bridge circuit having said first and second capacitors connected in associated legs thereof; and
a signal generator connected to and generating an input signal at an input of said bridge circuit, said bridge circuit being balanced when non-aerated lubricating fluid is flowing in said lubrication path and being unbalanced when aerated lubricating fluid is flowing in said lubrication path.

14. The aeration sensing system according to claim 13 wherein said sensor body is formed of a plastic material.

15. The aeration sensing system according to claim 13 wherein said signal generator is an oscillator.

16. The aeration sensing system according to claims 15 including a demodulator connected to an output of said bridge circuit for generating an output signal.

17. The aeration sensing system according to claim 13 wherein said plates of said first capacitor are first and second conductive rings positioned concentrically in said sensor body.

18. The aeration sensing system according to claim 17 wherein said plates of said second capacitor are said second conductive ring and a conductive segment positioned in said sensor body.

19. The aeration sensing system according to claim 18 wherein said first and second rings and said segment are formed of copper material.

20. An aeration sensing device for detecting aeration in a lubricating fluid comprising:
a non-conductive sensor body having opposed first and second ends;
a conductive first ring positioned within said sensor body, said first ring including a first wall;
a conductive second ring positioned within said sensor body and extending concentrically around said first ring, said second ring including a second wall adjacent to and spaced from said first wall to form a first gap, said first and second walls being plates of a first capacitor;
a lubrication flow path formed in said sensor body between said first and second ends and including said first gap; and
a conductive segment positioned within said sensor body radially outwardly from said second ring and including a third wall adjacent to and spaced from said second wall to form a second gap in fluid communication with said lubrication flow path, said second gap being in the form of a dead-end cavity, said second and third walls being plates of a second capacitor;
whereby when a lubricating fluid is introduced to said lubrication flow path at said first end, the lubricating fluid flows through said first gap to said second end and serves as a dielectric material defining a capacitance value for said first capacitor and further, when aerated lubricating fluid is flowing in said lubrication path, a portion of the aerated lubricating fluid flows into said second gap and becomes de-aerated serving as a dielectric material defining a capacitance value for said second capacitor.

21. The device according to claim 20 wherein said sensor body is generally cylindrical and said first and second rings extend about a longitudinal axis of said sensor body.

22. The device according to claim 21 including a first terminal electrically connected to said first ring, a second terminal electrically connected to said second ring and a third terminal electrically connected to said segment, said first through third terminals extending radially through said sensor body.

23. An aeration sensing device for detecting aeration in a lubricating fluid comprising:
a non-conductive sensor body having opposed first and second ends;
a conductive first ring positioned within said sensor body, said first ring including a first wall;
a conductive second ring positioned within said sensor body and extending concentrically around said first ring, said second ring including a second wall adjacent to and spaced from said first wall to form a first gap, said first and second walls being plates of a first capacitor, wherein said first ring has a radially outwardly extending terminal lug and said second wall has a slot formed therein receiving said terminal lug; and a lubrication flow path formed in said sensor body between said first and second ends and including said first gap, whereby when a lubricating fluid is introduced to said lubrication flow path at said first end, the lubricating fluid flows through said first gap to said second end and serves as a dielectric material defining a capacitance value for said first capacitor.

24. An aeration sensing device for detecting aeration in a lubricating fluid comprising:

a non-conductive sensor body having opposed first and second ends;

a conductive first ring positioned within said sensor body, said first ring including a first wall;

a conductive second ring positioned within said sensor body and extending concentrically around said first ring, said second ring including a second wall adjacent to and spaced from said first wall to form a first gap, said first and second walls being plates of a first capacitor; and a lubrication flow path formed in said sensor body between said first and second ends and including said first gap, wherein said sensor body has a central aperture formed Therein permitting the lubricating fluid to flow from said second end to said first end of said sensor body;

whereby when a lubricating fluid is introduced to said lubrication flow path at said first end, the lubricating fluid flows through said first gap to said second end and serves as a dielectric material defining a capacitance value for said first capacitor.

25. The device according to claim 24 including a conduit extending through said central aperture, a first end of said conduit adapted to attach to a filtration device mount and a second end of said conduit adapted to attach to a filtration device.

26. An aeration sensing device for detecting aeration in a fluid comprising:

a non-conductive sensor body having opposed first and second ends;

a conductive first ring positioned within said sensor body, said first ring including a first wall;

a conductive second ring positioned within said sensor body and extending concentrically around said first ring, said second ring including a second wall adjacent to and spaced from said first wall to form a first gap, said first and second walls being plates of a first capacitor;

wherein said first ring has a radially outwardly extending terminal lug and said second wall has a slot formed therein receiving said terminal lug, and a fluid flow path formed in said sensor body between said first and second ends and including through said first gap, whereby when a fluid is introduced to said fluid flow path, the fluid flows through said first gap to said second end and serves as a dielectric material defining a capacitance value for said first capacitor.

27. An aeration sensing device for detecting aeration in a fluid comprising:

a non-conductive sensor body having opposed first and second ends; wherein said sensor body has a central aperture formed therein permitting the fluid to flow from said second end to said first end of said sensor body, a conductive first ring positioned within said sensor body, said first ring including a first wall;

a conductive second ring positioned within said sensor body and extending concentrically around said first ring, said second ring including a second wall adjacent to and spaced from said first wall to form a first gap, said first and second walls being plates of a first capacitor; and a fluid flow path formed in said sensor body between said first and second ends and including through said first gap, whereby when a fluid is introduced to said fluid flow path, the fluid flows through said first gap to said second end and serves as a dielectric material defining a capacitance value for said first capacitor.

28. The device according to claim 27 including a conduit extending through said central aperture, a first end of said conduit adapted to attach to a filtration device mount and a second end of said conduit adapted to attach to a filtration device.

* * * * *